(12) United States Patent
Baweja et al.

(10) Patent No.: US 9,480,681 B2
(45) Date of Patent: Nov. 1, 2016

(54) CONTROLLED RELEASE FORMULATIONS OF NISOLDIPINE

(75) Inventors: Jitendra Mohansingh Baweja, Maharashtra (IN); Manoj Kumar Thottasseri, Maharashtra (IN); Sandip Tanaji Salunkhe, Maharashtra (IN); Mukund Keshav Gurjar, Maharashtra (IN); Samit Satish Mehta, Maharashtra (IN)

(73) Assignee: Emcure Pharmaceuticals Limited (IN)

( * ) Notice: Subject to any disclaimer, the term of this patent is extended or adjusted under 35 U.S.C. 154(b) by 0 days.

(21) Appl. No.: 14/344,835

(22) PCT Filed: Sep. 5, 2012

(86) PCT No.: PCT/IN2012/000583
§ 371 (c)(1),
(2), (4) Date: Mar. 13, 2014

(87) PCT Pub. No.: WO2013/098831
PCT Pub. Date: Jul. 4, 2013

(65) Prior Publication Data
US 2014/0341990 A1 Nov. 20, 2014

(30) Foreign Application Priority Data

Sep. 23, 2011 (IN) .......................... 2699/MUM/2011

(51) Int. Cl.
| | | |
|---|---|---|
| *A61K 9/14* | (2006.01) | |
| *A61K 31/4422* | (2006.01) | |
| *A61K 9/28* | (2006.01) | |
| *A61K 9/20* | (2006.01) | |

(52) U.S. Cl.
CPC ............ *A61K 31/4422* (2013.01); *A61K 9/14* (2013.01); *A61K 9/2018* (2013.01); *A61K 9/2031* (2013.01); *A61K 9/2054* (2013.01); *A61K 9/2095* (2013.01); *A61K 9/2846* (2013.01); *A61K 9/2866* (2013.01); *A61K 9/2013* (2013.01); *A61K 9/2027* (2013.01); *A61K 9/2853* (2013.01)

(58) Field of Classification Search
CPC ............ A61K 9/2013; A61K 9/2054; A61K 9/2031; A61K 31/4422
See application file for complete search history.

(56) References Cited

U.S. PATENT DOCUMENTS

| | | | |
|---|---|---|---|
| 2003/0157326 A1* | 8/2003 | Vaghefi et al. ............ | 428/402.2 |
| 2008/0221174 A1* | 9/2008 | Grenier et al. ............... | 514/356 |
| 2010/0247646 A1* | 9/2010 | Prasad ................. | A61K 9/2054 424/468 |

FOREIGN PATENT DOCUMENTS

WO WO 2010060564 A1 * 6/2010

OTHER PUBLICATIONS

Translation of WO2010060564 retrieved from WIPO (https://patentscope.wipo.int/search/en/search.jsf) on Mar. 2, 2015.*

* cited by examiner

*Primary Examiner* — Jessica Worsham
(74) *Attorney, Agent, or Firm* — Florek & Endres PLLC

(57) ABSTRACT

Controlled release oral dosage formulations containing calcium channel blocker and processes for preparation thereof, are provided for once a day treatment. The active agent is preferably a dihydropyridine calcium channel blocker, such as nisoldipine. In one embodiment, the formulation provides controlled release of micronized nisoldipine with one or more pH independent release controlling polymers. The controlled release matrix formulation is advantageous and can be prepared by a simple, economically viable process as compared to complex core-coat prior-art versions.

10 Claims, No Drawings

CONTROLLED RELEASE FORMULATIONS OF NISOLDIPINE

This application is a U.S. National Stage filing under 35 U.S.C §371 of International Application No. PCT/IN2012/00583, filed Sep.5, 2012, which in turn claims priority to Indian Patent Application No. 2699/MUM/2011, filed Sep. 23, 2011.

FIELD OF THE INVENTION

The present invention relates to a controlled release tablet formulation of nisoldipine and to processes for their preparation thereof.

BACKGROUND OF THE INVENTION

Nisoldipine, chemically known as 3,5-pyridinedicarboxylic acid-1,4-dihydro-2,6-dimethyl-4-(2-nitrophenyl)-methyl-2-methyl-propyl ester, belongs to the dihydropyridine class of calcium channel blockers and is approved for the treatment of hypertension, either alone or in combination with other antihypertensive agents.

Nisoldipine was first disclosed by Wehinger et al in U.S. Pat. No. 4,154,839 and is marketed in USA and worldwide under the brand name SULAR® as an extended release formulation. Initially, the marketed extended release oral formulations of SULAR® were available in 10, 20, 30 and 40 mg strengths. However, subsequently these formulations were replaced with a lower strength formulation of Nisoldipine and presently the marketed nisoldipine formulations are available as extended release tablets in 8.5, 17, 25.5 and 34 mg strengths. These are available as multi-layered tablets with top and bottom barrier layers and a middle layer of active ingredient, Nisoldipine.

Dihydropyridines pharmaceuticals such as nisoldipine, which have very low solubility in water, pose serious difficulties in preparation of formulations. This is attributed to their poor rate and extent of dissolution in aqueous media and gastrointestinal fluids, which ultimately results in low absorption in the systemic circulation after oral ingestion.

Therefore, different approaches have been used in the prior art for making formulations of sparingly soluble dihydropyridines such as nisoldipine. Ohm et al in U.S. Pat. No. 4,892,741 discloses a press coated tablet comprising a core which contains dihydropyridine in a rapid release form and a coat around it with a dihydropyridine in a slow release form.

Conte et al in U.S. Pat. No. 5,626,874 discloses a controlled release pharmaceutical tablet, having a lenticular form consisting of the three over-imposed layers. The disclosed formulation has a central layer or core comprising an active principle and two external barrier layers upon and under said core layer limiting the active principle release.

Vergnault et al in WO2008/025535 discloses a multi layered controlled release oral dosage formulation for Nisoldipine wherein the core contained the active ingredient along with an enteric agent while the barrier layers comprised swellable, gellable or erodible polymers.

Maggi et al in U.S. Pat. No. 6,221,395 discloses a pharmaceutical tablet for oral administration, which is able to release under controlled speed, the active principles having low solubility. The document discloses use of particular concentrations of surface active agents in a hydrophilic matrix in order to enhance the dissolution speed of a poorly soluble drug and one or more barrier layer surrounding the active layer.

Further, Prasad et al in US 2010/247646 discloses an extended release tablet comprising a core of nisoldipine, a hydrophilic polymer optionally, an enteric agent and a release rate-controlling coating comprising a hydrophobic polymer, an enteric agent or a combination thereof surrounding the said core.

Thus, the prior art formulations exhaustively relates to multilayer tablet formulations which comprise a top barrier layer, a middle layer containing active therapeutic agent and a bottom barrier layer for preparing an extended release formulation of nisoldipine. Although, these formulations can provide an extended release formulation, but the requirement of complex machinery and processing for tableting renders their manufacturing, an expensive and time-consuming process making them commercially not particularly viable.

Therefore, there exists a need for an extended release formulation for nisoldipine which is convenient and simple to manufacture.

OBJECT OF THE INVENTION

It is therefore an object of the present invention to provide a simple controlled release formulation for sparingly water soluble drugs such as dihydropyridines.

Another object of the present invention is to provide a simple controlled release formulation of nisoldipine.

Yet another object of the present invention is to provide a simple, economically viable process for preparation of controlled release formulation of nisoldipine.

SUMMARY OF THE INVENTION

The present inventors have surprisingly found that a controlled release oral dosage formulation containing nisoldipine could be prepared without taking recourse to a complex technology of manufacturing a central layer containing active ingredient and various barrier layers surrounding the said central layer.

Moreover, it was found that release rate of the formulation is influenced by the addition of auxiliaries with good water solubility and by alteration of the particle size distribution of the active compound. Therefore, in the present invention the desired controlled release profile of dihydropyridines could be achieved by using micronized crystalline form of active compound and one or more pH independent release controlling polymers.

In a preferred embodiment of the present invention, the controlled release formulation comprises micronized nisoldipine and pH independent release controlling polymer. The controlled release formulation is a tablet containing dihydropyridine calcium channel blocker, such as nisoldipine in micronized crystalline form and one or more polymeric materials that modulate the release of nisoldipine.

The release controlling polymer is selected from various hydrophilic polymers or combinations thereof. The concentration of the polymeric material is from about 1% to about 60% by weight of the tablet, preferably from about 10% to about 40% by weight of the tablet.

The tablet may also contain one or more adjuvants, which, in combination with the polymeric materials, may help to further modulate the release of nisoldipine. The concentration of the adjuvant(s) is from about 1% to about 40% by weight of the compositions, preferably from about 5% to about 25% by weight of the composition. The tablet also contains conventional tableting excipients, such as, diluents, binders, disintegrants, lubricants, glidants, anti-adherents, stabilizing agents and combinations thereof.

The judicious selection of particle size of nisoldipine, the release controlling polymers, excipients as well as the ratio of the same used in the pharmaceutical composition of the present invention, result in a formulation which allows micronized nisoldipine to be released in a controlled manner for absorption into the circulatory system. Thus, typically, the present formulation is not critically dependent on vagaries of functional layers present in the multilayer formulations of the prior art, which act as a barrier for release of the drug.

Thus, in one aspect, the present invention provides a controlled release solid dosage form, preferably in the form of a tablet, comprising nisoldipine. Further, the present invention also provides a process to prepare such a controlled release composition.

DETAILED DESCRIPTION OF THE INVENTION

The present invention relates to a controlled release matrix formulation comprising nisoldipine and one or more pH independent release controlling polymers.

As used herein the term "controlled release" formulation means a dosage form in which the release of the active agent is controlled or modified over a period of time. Controlled can mean, for example, extended, sustained, delayed, prolonged or pulsed-release at a particular time. Moreover, controlled can mean that the release of the active agent is extended for longer time than that from an immediate-release dosage form having same amount of active agent.

The composition of the present invention typically includes the micronized nisoldipine. Particle size distribution and surface properties can be critical factors affecting the release of the active agent from the dosage form. In general, a person skilled in the art would expect that particle size reduction of poorly soluble compound would result in better dissolution and hence increased bioavailability of the compound. To increase the release rate of the active agent from the suspended particles, various size reduction techniques can be applied. Typically, processes like grinding, milling, micronization, and nanosizing are well known in the art and can be utilized to obtain a mean particle size from several tens of micrometers to a tenth of a micrometer. But, in the present case, release from the formulation could be better controlled by judicious selection of particle size range and pH independent release controlling polymer. In a preferred embodiment of the present invention, mean particle size of micronized nisoldipine is in the range of about 5 µm about 25 µm, preferably of about 10 µm.

Preferably, the invention relates to an extended release tablet formulation, wherein the micronized nisoldipine is embedded in a matrix comprising pH independent release controlling polymer. The matrix systems for controlled release preparations are well known in the art. The drug in a matrix system is homogenously dispersed in a polymer in association with conventional excipients and drug is released from this tablet by diffusion and/or erosion.

The term "pH independent release controlling polymer" as used herein includes, but not limited to, the polymers and agents that swell and/or gel in the aqueous media. The pH independent release controlling polymers suitable for use according to present invention include hydrophilic polymers such as alkylcelluloses, such as methylcellulose; hydroxyalkylcelluloses, for example, hydroxymethyl cellulose, hydroxyethyl cellulose, hydroxypropyl cellulose and hydroxybutylcellulose; hydroxyalkyl alkylcelluloses, such as hydroxyethyl methylcellulose and hydroxypropyl methylcellulose; carboxyalkylcelluloses, such as carboxymethylcellulose; alkali metal salts of carboxyalkylcelluloses, such as sodium carboxymethylcellulose; carboxyalkyl alkylcelluloses, such as carboxymethyl ethylcellulose; carboxyalkylcellulose esters; other natural, semi-synthetic, or synthetic polysaccharides and gums, such as alginic acid, alkali metal and ammonium salts thereof, carrageenans, galactomannans, tragacanth, agar-agar, gum arabic, guar gum, xanthan gum, starches, pectins, such as sodium carboxymethyl amylopectin, chitin derivates, such as chitosan, polyfructans, inulin; polyacrylic acids and the salts thereof; polymethacrylic acids and the salts thereof, methacrylate copolymers; polyvinylalcohol; polyvinylpyrrolidone, copolymers of polyvinylpyrrolidone with vinyl acetate; combinations of polyvinylalcohol and polyvinylpyrrolidone; polyalkylene oxides, such as polyethylene oxide and polypropylene oxide and copolymers of ethylene oxide and propylene oxide or combinations thereof. In a particular embodiment, the hydrophilic polymer(s) are the alkyl celluloses, like hydroxypropyl methylcellulose. More preferably, the hydroxypropyl methyl cellulose polymers having viscosity in the range of 400-10000 cps are preferred.

The amount of the polymer in the dosage form generally varies from about 1% to about 60% by weight of the composition. Preferably, the amount of polymers varies from about 10% to about 40% by weight of the dosage form. Most preferably, the amount of polymer varies from about 15% to about 30% by weight of the dosage form.

Optionally, along with pH independent release controlling polymer, the tablet of the present invention may comprise of an enteric agent, which may further help in providing the desired drug release profile from the extended release tablet. The enteric agent may include cellulose polymers, such as cellulose acetate phthalate, hydroxypropyl cellulose phthalate, hydroxypropyl methylcellulose phthalate and hydroxypropyl methylcellulose acetate succinate; polyvinyl acetate phthalate, acrylic acid polymers and copolymers, and methacrylic polymers and copolymers that are commercially available under the trade name Eudragit® (Evonik-Degussa), such as copolymers of ethyl acrylate, methyl methacrylate with a low content of a methacrylic acid ester with a quaternary ammonium groups (trimethyl ammonioethyl methacrylate chloride) (Eudragit® RS100 and Eudragit® RL100) and poly(ethylacrylate-methylmethacrylate) (Eudragit® NE) and Poly (Methacrylic acid-co-methyl methacrylate) (Eudragit L 100); alginates, alkali-soluble acrylic resins, hydroxypropyl methylcellulose phthalate, methacrylate-methacrylic acid co-polymers, polyvinyl acetate phthalate, styrol maleic acid copolymers, and the like, and combinations thereof. The amount of the enteric agent that may be present in the core is from about 0.1% (w/w) to about 25% (w/w) by total weight of the tablet.

The composition of the invention also typically includes pharmaceutically acceptable excipients. As is well known to those skilled in the art, pharmaceutical excipients are routinely incorporated into solid dosage forms. This is done to ease the manufacturing process as well as to improve the performance of the dosage form. Common excipients include diluents or bulking agents, lubricants, binders, solubilizers etc. Such excipients are routinely used in the dosage forms of this invention.

Diluents, or fillers, are added in order to increase the mass of an individual dose to a size suitable for tablet compression. Suitable diluents include powdered sugar, calcium phosphate, calcium sulfate, microcrystalline cellulose, lactose, mannitol, kaolin, sodium chloride, dry starch, sorbitol, etc.

Lubricants are incorporated into a formulation for a variety of reasons. They reduce friction between the granulation and die wall during compression and ejection. This prevents the granulated material from sticking to the tablet punches, thereby facilitating its ejection from the tablet punches, etc. Examples of suitable lubricants include talc, stearic acid, vegetable oil, calcium stearate, zinc stearate, magnesium stearate, etc.

Glidants are also typically incorporated into the formulation. A glidant improves the flow characteristics of the granulation. Examples of suitable glidants include talc, silicon dioxide and cornstarch.

Binders may be incorporated into the formulation. Binders are typically utilized if the manufacture of the dosage form uses a granulation step. Examples of suitable binders include povidone, polyvinylpyrrolidone and xanthan gum, cellulose gums such as carboxymethylcellulose, methyl cellulose, hydroxypropylmethylcellulose, hydroxycellulose, gelatin, starch and pregelatinized starch.

Suitable solubilizer(s) that may be used include sodium, potassium, ammonium of long chain alkyl sulfonates and alkyl aryl sulfonates, such as sodium dodecylbenzene sulphonate; dialkyl sodium sulphosuccinates; dialkyl sodium sulfosuccinates; alkyl sulphates, such as sodium lauryl sulphate; PEG-150 laurate; PEG-400 monolaurate; polyoxyethylene monolaurate; polysorbates; polyethoxylated castor oil (e.g. Cremophor®), benzalkonium chloride; benzethonium chloride; cetriammonium bromide, stearyl dimethylbenzyl ammonium chloride, ethylene glycol monostearate, propylene glycol myristate, glyceryl monostearate, glyceryl stearate, polyglyceryl-4-oleate, sorbitan acylate, sucrose acylate, polyoxyethylene octylphenylether, PEG-1000 cetyl ether, polyoxyethylene tridecyl ether, polypropylene glycol butyl ether, Poloxamer®, stearoyl monoisopropanolamide, polyoxyethylene hydrogenated tallow amide, sodium N-dodecyl-β-alanine, sodium N-lauryl-β-iminodipropionate, myristoamphoacetate, lauryl betaine and lauryl sulfobetaine.

Other excipients that may be incorporated into the formulation include preservatives, antioxidants, or any other excipient commonly used in the pharmaceutical industry, etc. The amount of excipients in the formulation will correspond to that typically used in a matrix system. The total amount of excipients, fillers and extenders, etc. varies from about 10% to about 80% by weight of the dosage form.

The matrix formulations are generally prepared using standard techniques well known in the art. Typically, they are prepared by dry blending the hydrophilic polymer, filler, nisoldipine and other excipients followed by granulating the mixture using suitable solvent, such as alcohol, until proper granulation is obtained. The granulation is done by methods known in the art. The wet granules are dried in a fluid bed dryer, sifted and ground to appropriate size. Lubricating agents are mixed with the dried granulation to obtain the final formulation. Suitable granulating solvents that may be used according to the present invention include water, ethanol, methanol, isopropyl alcohol, methylene chloride, acetone, and combinations or equivalents thereof.

The compositions of the invention can be administered orally in the form of tablets, pills, or the granulate may be loose filled into capsules. The tablets can be prepared by techniques known in the art and contain a therapeutically useful amount of the nisoldipine and such excipients as are necessary to form the tablet by such techniques.

The formulation of the present invention may be optionally coated with one or more modified release coatings, which further modulate the release of the active agent from the core or central layer. Suitable coatings include taste mask coatings, enteric coatings, sustained or extended release coatings and delayed release coatings. The dosage forms may also be coated for aesthetic reasons such as to impart a color to the dosage form or to apply a surface finish to the dosage form. The coating liquid generally comprises film forming polymers such as hydroxypropyl cellulose, hydroxypropylmethyl cellulose, cellulose esters or ethers (such as cellulose acetate or ethylcellulose), an acrylic polymer or a mixture of polymers.

The coating solution is generally an aqueous solution or an organic solvent further comprising propylene glycol, sorbitan monoleate, sorbic acid. The coating composition may further comprise of one or more additives including water soluble agents, pore forming agents, plasticizers, coloring agents, anti-tacking agents, lubricants/glidants and other conventionally used coating additives.

Suitable water soluble agent(s) that may be used include cellulosic polymers, such as hydroxypropyl methylcellulose; polyvinylpyrrolidone; vinyl acetate copolymers; starch and starch based polymers; polysaccharides; or a mixture thereof.

Suitable pore forming agents that may be used include water-soluble compounds and hydrophilic polymers, and may include alkali metal salts, e.g. sodium chloride, sodium bromide and the like; alkaline earth metals, e.g. calcium phosphate, calcium nitrate and the like; transition metal salts, e.g. ferric chloride, ferrous sulfate and the like; polyglycols; ethyl vinyl alcohols; glycerin; pentaerythritol; polyvinyl alcohols; vinylpyrrolidone; N-methyl pyrrolidone; saccharides; hydrolyzed starch; pregelatinized starch; carbohydrates, for e.g. glyceraldehydes, erythrose, ribose, arabinose, xylose, glucose, mannose, galactose, maltose, lactose, sucrose and the like; and sugar alcohols, e.g. mannitol and the like. Hydrophilic polymer(s) that may be used as a pore forming agent may include hydroxypropyl cellulose, hydroxypropyl methylcellulose, polyvinylpyrrolidone and the like.

Suitable plasticizers include dibutyl sebacate, polyethylene glycol, triethyl citrate, triacetin, acetylated triacetin, tributyl citrate, glycerol tributyrate, natural, semi-synthetic and synthetic glycerides, monoglyceride, acetylated monoglycerides, fractionated coconut oil, rape oil, olive oil, sesame oil, castor oil, hydrogenated castor oil, acetyltributylcitrate, acetyltriethylcitrate, glycerin sorbitol, diethyl oxalate, diethyl phthalate, diethyl malate, diethyl fumarate, dibutyl succinate, diethyl malonate, dioctyl phthalate, and the like.

The extended release tablet of the present invention may be optionally coated with a non-functional coating. The non-functional coating may additionally include one or more pharmaceutically acceptable colourants or opacifiers, including water soluble dyes, aluminium lakes of water soluble dyes and inorganic pigments such as titanium dioxide and iron oxide. It may also contain one or more plasticizing agents conventionally used in polymeric film coatings, for example, polyethylene glycol, propylene glycol, dibutyl sebacate, mineral oil, sesame oil, diethyl phthalate and triacetin. Proprietary non-functional coating materials, such as OPASPRAY® and OPADRY®, obtainable from Colorcon Limited, UK, may also be used.

A particularly preferred matrix system for the extended release preparation of the nisoldipine comprises: from about 5 weight percent to about 20 weight percent of micronized nisoldipine; from about 10 weight percent to about 30 weight percent of hydroxypropyl methylcellulose; from about 2 weight percent to about 6 weight percent of methacrylic acid copolymer; from about 30 weight percent to about 60 weight percent of lactose, from about 5 weight percent to about 10 weight percent of sodium lauryl sulfate and from about 0.1 weight percent to about 5 weight percent of silicon dioxide and all weight percentages based upon the total weight of the dosage form.

More specifically, a nisoldipine matrix may typically be prepared by (a) dry blending a mixture of from about 5 weight percent to about 15 weight percent nisoldipine having particle size less than 40 microns, from about 10 weight percent to about 25 weight percent hydroxypropylmethyl cellulose, from about 2 weight percent to about 4 weight percent of methacrylic acid copolymer; from about 50 weight percent to about 60 weight percent lactose to form a uniform mixture of the dry ingredients;

(b) wet granulating the dry uniform mixture from step a) with povidone binder solution;

(c) drying and sizing the wet granules from step b) to select granules having the desired average size;

(d) dry blending the granules with silicon dioxide and magnesium stearate; and (e) compressing the blended granules of step d) to get the tablet; and (f) Optionally coating with a suitable polymer along with plasticizer cum pore forming agent.

The principles, preferred embodiments, and modes of operation of the present invention have been described in the foregoing specification. The invention which is intended to be protected herein, however, is not to be construed limited to the particular forms disclosed, since these are to be regarded as illustrative rather than restrictive. Variations and changes may be made by those skilled in the art, without departing from the spirit of the invention.

The invention is further explained with the help of following illustrative examples, however, in no way these examples should be construed as limiting the scope of the invention.

ILLUSTRATIVE EXAMPLES

Example—1

Two identical formulations using unmicronized or micronized 34 mg of Nisoldipine were prepared. The formulations are identified as Formulation A and Formulation B and are described in Table 1. Tablets are prepared by dry blending the hydrophilic polymer Methocel K4MCR, lactose nisoldipine, sodium lauryl sulfate and Methacrylic acid copolymer followed by granulating the mixture using povidone binder solution, until proper granulation is obtained. The wet granules are dried in a fluid bed dryer, sifted and ground to appropriate size. Lubricating agents are mixed with the dried granulation to obtain the final formulation. The tablets of formulation A and formulation B were subjected to dissolution studies in a USP II apparatus in 900 mL of 0.03N hydrochloric acid with 0.5% sodium lauryl sulphate. The temperature and agitation were set at 37° C.±0.5° C. and 50 rpm, respectively. Dissolution profiles of these tablets are provided in Table 2.

TABLE 1

Nisoldipine Tablet Composition

| Sr. No. | Ingredients | Formulation - A (unmicronized API) mg/Tablet | Formulation - B (micronized API) Mg/tablet |
|---|---|---|---|
| 1. | Nisoldipine | 34.0 | 34.0 |
| 2. | Lactose Monohydrate | 361.6 | 361.6 |
| 3. | Sodium Lauryl Sulphate | 30.0 | 30.0 |
| 4. | Methacrylic acid copolymer Type A | 21.4 | 21.4 |
| 5. | Methocel K4MCR | 120.0 | 120.0 |
| 6. | PVP K30 | 24.0 | 24.0 |
| 7. | Purified water | QS | QS |
| 8. | Colloidal Silicon Dioxide | 3.0 | 3.0 |
| 9. | Magnesium Stearate | 6.0 | 6.0 |
| | Total Tablet weight (mg) | 600.0 | 600.0 |

TABLE 2

Dissolution profile of the tablets of Formulation A and Formulation B
Dissolution Condition
RPM 50, 900 mL, 0.03N HCl with 0.5% SLS Apparatus USP II

| Time in Hrs | % drug release (Avg) | |
|---|---|---|
| | Formulation A | Formulation B |
| 1.0 | 4.5 | 4.2 |
| 2.0 | 9.2 | 10.0 |
| 4.0 | 19.6 | 22.8 |
| 8.0 | 41.5 | 50.8 |
| 12.0 | 60.5 | 76.3 |
| 15.0 | 73.2 | 88.8 |
| 18.0 | 80.9 | 96.8 |
| 24.0 | 83.2 | 99.3 |

Example—2

Three identical formulations using various grades of hydroxypropyl methyl cellulose varying in viscosity were prepared. The formulations are identified as Formulation C, Formulation D and Formulation E and are described in Table 3. The tablets of these formulations were subjected to dissolution studies in a USP II apparatus in 900 mL of 0.03N hydrochloric acid with 0.5% sodium lauryl sulphate. The temperature and agitation were set at 37° C.±0.5° C. and 50 rpm, respectively. Dissolution profiles of these tablets are provided in Table 4.

TABLE 3

Nisoldipine Tablet Compositions using various grades of hydroxypropyl methyl cellulose varying in viscosity

| | | mg/Tablet | | |
|---|---|---|---|---|
| Sr. No. | Ingredients | Formulation C | Formulation D | Formulation E |
| 1. | Nisoldipine | 34.0 | 34.0 | 34.0 |
| 2. | Lactose Monohydrate | 349.1 | 433.1 | 433.1 |
| 3. | Sodium Lauryl Sulphate | 42.5 | 42.5 | 42.5 |
| 4. | Methacrylic acid copolymer Type A | 21.4 | 21.4 | 21.4 |
| 5. | Hypromellose (4000 cps) Methocel K4 MCR | 120.0 | — | — |
| | Hypromellose (15000 cps) Methocel K15 Premium CR | — | 42.0 | — |
| | Hypromellose (100000 cps) Methocel K100 Premium CR | — | — | 30.0 |

TABLE 3-continued

Nisoldipine Tablet Compositions using various grades
of hydroxypropyl methyl cellulose varying in viscosity

|  |  | mg/Tablet | | |
|---|---|---|---|---|
| Sr. No. | Ingredients | Formulation C | Formulation D | Formulation E |
| 6. | Povidone K30 | 24.0 | 24.0 | 24.0 |
| 7. | Purified water | QS | QS | QS |
| 8. | Colloidal Silicon Dioxide | 3.0 | 3.0 | 3.0 |
| 9. | Magnesium Stearate | 6.0 | 6.0 | 6.0 |
|  | Total Tablet weight (mg) | 600.0 | 600.0 | 600.0 |

TABLE 4

Dissolution profile of Formulation C,
Formulation D and Formulation E Tablets
Dissolution Condition
RPM 50, 900 mL, 0.03N HCl
with 0.5% SLS Apparatus USP II

|  | % drug release (Avg) | | |
|---|---|---|---|
| Time in Hrs | Formulation C | Formulation D | Formulation E |
| 1.0 | 4.8 | 3.0 | 3.9 |
| 2.0 | 10.0 | 10.7 | 11.0 |
| 4.0 | 19.5 | 18.9 | 16.9 |
| 8.0 | 48.5 | 50.0 | 49.8 |
| 12.0 | 73.2 | 74.8 | 72.9 |
| 15.0 | 88.8 | 87.9 | 84.5 |
| 18.0 | 92.2 | 93.2 | 93.5 |
| 24.0 | 96.0 | 95.7 | 97.0 |

Example—3

Nisoldipine tablets were prepared by using various hydrophilic polymers to see the effect of various polymer on Nisoldipine release from the tablet. The polymers evaluated in this study include hydroxypropyl cellulose (Formulation F), hydroxyethyl cellulose (Formulation G), and Polyethylene oxide (Formulation H), as summarized in Table 5. The tablets of these formulations were subjected to dissolution studies in a USP II apparatus in 900 mL of 0.03N hydrochloric acid with 0.5% sodium lauryl sulphate. The temperature and agitation were set at 37° C.±0.5° C. and 50 rpm, respectively. Dissolution profiles of these tablets are provided in Table 6.

TABLE 5

Nisoldipine Tablet Compositions using
various hydrophilic polymers

|  |  | mg/Tablet | | |
|---|---|---|---|---|
| Sr. No. | Ingredients | Formulation F | Formulation G | Formulation H |
| 1. | Nisoldipine | 34.0 | 34.0 | 34.0 |
| 2. | Lactose Monohydrate | 349.1 | 369.1 | 379.1 |
| 3. | Sodium Lauryl Sulphate | 42.5 | 42.5 | 42.5 |
| 4. | Methacrylic acid copolymer Type A | 21.4 | 21.4 | 21.4 |
| 5. | Hydroxypropylcellulose EXF | 120 | — | — |
|  | Hydroxyethyl cellulose | — | 100.0 | — |
|  | Polyethylene oxide (Polyox WSR 205 NF) | — | — | 90 |
| 6. | Povidone K30 | 24.0 | 24.0 | 24.0 |
| 7. | Purified water | QS | QS | QS |
| 8. | Colloidal Silicon Dioxide | 3.0 | 3.0 | 3.0 |
| 9. | Magnesium Stearate | 6.0 | 6.0 | 6.0 |
|  | Total Tablet weight (mg) | 600.0 | 600.0 | 600.0 |

TABLE 6

Dissolution profile of Formulation F,
Formulation G and Formulation H Tablets
Dissolution Condition
RPM 50, 900 mL, 0.03N HCl
with 0.5% SLS Apparatus USP II

| Time | % drug release (Avg) | | |
|---|---|---|---|
| in Hrs | Formulation F | Formulation G | Formulation H |
| 1.0 | 5.1 | 3.9 | 2.0 |
| 2.0 | 16.0 | 14.8 | 12.1 |
| 4.0 | 25.4 | 26.8 | 22.0 |
| 8.0 | 56.2 | 52.4 | 50.7 |
| 12.0 | 79.8 | 78.0 | 77.2 |
| 15.0 | 90.0 | 90.0 | 90.0 |
| 18.0 | 94.7 | 93.8 | 94.9 |
| 24.0 | 97.5 | 97.9 | 97.8 |

Example—4

To determine the effect of enteric coating, nisoldipine tablets prepared according to present invention were coated using hypromellose phthalate (Formulation I) and Eudragit polymer (Formulation J). The compositions are summarized in Table 7. The tablets of these formulations were subjected to dissolution studies in a USP II apparatus. Dissolution profiles of these tablets are provided in Table 8.

TABLE 7

Nisoldipine Tablet Compositions
coated with enteric coating polymer

|  |  | mg/Tablet | |
|---|---|---|---|
| Sr. No. | Ingredients | Formulation I | Formulation J |
| 1. | Nisoldipine | 34.0 | 34.0 |
| 2. | Lactose Monohydrate | 385.6 | 385.6 |
| 3. | Sodium Lauryl Sulphate | 30.0 | 30.0 |
| 4. | Methacrylic acid copolymer Type A | 21.4 | 21.4 |
| 5. | Methocel K4MCR | 120.0 | 120.0 |
| 6. | PVP K30 | 24.0 | 24.0 |
| 7. | Purified water | QS | QS |
| 8. | Colloidal Silicon Dioxide | 3.0 | 3.0 |
| 9. | Magnesium Stearate | 6.0 | 6.0 |
|  | Total Tablet weight (mg) | 600.0 | 600.0 |
| 10. | Hypromellose phthalate (HPMCP HP 50) | 16.2 | — |
|  | Eudragit L30 D55 | — | 21.00 |
| 11. | PEG 400 | 1.8 | — |
|  | PEG 6000 | — | 2.1 |
| 12. | Solvent | Qs | Qs |

TABLE 8

Dissolution profile of Formulation I
and Formulation J Tablets
Dissolution Condition
RPM 50, 900 mL, 0.03N HCl
with 0.5% SLS Apparatus USP II

| Time | % drug release (Avg) | |
|---|---|---|
| in Hrs | Formulation I | Formulation J |
| 1.0 | 0.3 | 0 |
| 2.0 | 5.2 | 4.0 |
| 4.0 | 15.1 | 15.2 |
| 8.0 | 40.2 | 40.5 |
| 12.0 | 79.0 | 78.9 |
| 15.0 | 87.1 | 88.0 |
| 18.0 | 92.8 | 91.6 |
| 24.0 | 98.2 | 93.4 |

The invention claimed is:

1. A controlled release matrix tablet formulation consisting of:
   i. a tablet core; and
   ii. optionally a non-functional or aesthetic coating,
   wherein the tablet core is a mixture comprising:
   a. micronized nisoldipine with a mean particle size in the range of about 5 μm to about 25 μm;
   b. about 1 wt % to about 60 wt % of one or more hydrophilic pH independent release controlling polymers;
   c. about 0.1 wt % to about 25 wt % of an enteric agent selected from the group consisting of cellulose acetate phthalate, hydroxypropyl cellulose phthalate, hydroxypropyl methylcellulose phthalate, hydroxypropyl methylcellulose acetate succinate, polyvinyl acetate phthalate, acrylic acid polymers and copolymers, methacrylic polymers and copolymers, alginates, alkali-soluble acrylic resins, methacrylate-methacrylic acid copolymers, polyvinyl acetate phthalate, styrol maleic acid copolymers, and combinations thereof; and
   d. tableting excipients selected from the group consisting of diluents, fillers, binders, surfactants, solubilizers, lubricants, glidants and combinations thereof
   wherein the controlled release matrix tablet releases about 10% to about 16% of the nisoldipine after two hours, about 16.9% to about 25.4% after 4 hours, and about 48.5% to about 56.2% after 8 hours of in vitro testing using a USP Type II dissolution apparatus operated at 50 rpms and with 900 ml of 0.03 N HCl with 0.5% sodium lauryl sulfate.

2. The controlled release matrix tablet formulation according to claim 1, wherein the hydrophilic pH independent release controlling polymer is hydroxypropyl methylcellulose.

3. The controlled release matrix tablet formulation of claim 1 wherein the tablet core comprises:
   a) from about 5 weight percent to about 20 weight percent of micronized nisoldipine;
   b) from about 10 weight percent to about 30 weight percent of one or more hydrophilic pH independent release controlling polymers;
   c) from about 2 weight percent to about 6 weight percent of an enteric agent methacrylic acid copolymer;
   d) from about 30 weight percent to about 60 weight percent of lactose;
   e) from about 5 weight percent to about 10 weight percent of sodium lauryl sulfate; and
   f) from about 0.1 weight percent to about 5 weight percent of silicon dioxide.

4. The controlled release matrix tablet formulation of claim 1, wherein the one or more hydrophilic pH independent release controlling polymers comprise from about 10% to about 40% by weight of the formulation.

5. The controlled release matrix tablet formulation of claim 1, wherein the one or more hydrophilic pH independent release controlling polymers comprise from about 15% to about 30% by weight of the formulation.

6. The controlled release matrix tablet formulation according to claim 1, wherein the micronized nisoldipine has a mean particle size of about 10 μm.

7. A controlled release matrix tablet formulation consisting essentially of:
   i. a tablet core; and
   ii. optionally a non-functional or aesthetic coating,
   wherein the tablet core is a mixture consisting essentially of:
   a. about 5 wt % to about 20 wt % micronized nisoldipine with a mean particle size in the range of about 5 μm to about 25 μm;
   b. about 10 wt % to about 30 wt % of one or more hydrophilic pH independent release controlling polymers;
   c. about 2 wt % to about 6 wt % of an enteric agent methacrylic acid copolymer;
   d. from about 30 wt % to about 60 wt % of lactose;
   e. from about 5 wt % to about 10 wt % of sodium lauryl sulfate; and
   f. from about 0.1 wt % to about 5 wt % of silicon dioxide
   and wherein the controlled release matrix tablet releases about 10% to about 16% of the nisoldipine after two hours, about 16.9% to about 25.4% after 4 hours, and about 48.5% to about 56.2% after 8 hours of in vitro testing using a USP Type II dissolution apparatus operated at 50 rpms and with 900 ml of 0.03 N HCl with 0.5% sodium lauryl sulfate.

8. A process for preparation of a controlled release nisoldipine formulation of claim 1 comprising:
   a) dry blending a mixture of nisoldipine, hydroxypropylmethyl cellulose, methacrylic acid copolymer, lactose and sodium lauryl sulfate to form a dry uniform mixture;
   b) wet granulating the dry uniform mixture with povidone binder solution to form wet granules;
   c) drying and sizing the wet granules;
   d) lubricating the granules with silicon dioxide and magnesium stearate to form blended granules; and
   e) compressing the blended granules into a tablet core.

9. A method of treating hypertension in a patient comprising the step of orally administering the controlled release matrix tablet formulation of claim 1 to the patient.

10. A method of treating hypertension in a patient comprising the step of orally administering the controlled release matrix tablet formulation of claim 3 to the patient.

* * * * *